United States Patent [19]

Dyer et al.

[11] Patent Number: 4,605,639

[45] Date of Patent: Aug. 12, 1986

[54] METHODS FOR MAKING A SUPPORTED IRON-COPPER CATALYST

[75] Inventors: Paul N. Dyer, Allentown; Ronald Pierantozzi, Macungie, both of Pa.

[73] Assignee: Air Products and Chemicals, Inc., Allentown, Pa.

[21] Appl. No.: 755,986

[22] Filed: Jul. 17, 1985

[51] Int. Cl.$^4$ .................. B01J 21/04; B01J 23/72; B01J 23/78

[52] U.S. Cl. .................... 502/331; 518/713

[58] Field of Search .................. 502/331; 518/713

[56] References Cited

U.S. PATENT DOCUMENTS

| | | | |
|---|---|---|---|
| 2,692,274 | 10/1954 | Kölbel et al. | 518/713 |
| 3,271,324 | 9/1966 | Stephens et al. | 502/331 |
| 3,759,825 | 9/1973 | Chun et al. | 502/331 X |
| 3,907,666 | 9/1975 | Chun et al. | 502/331 X |

OTHER PUBLICATIONS

"The Fischer-Tropsch and Related Syntheses", Storch & Golumbic (H. H. Storch, N. Golumbic, R. B. Anderson).

*Catal. Rev. Sci. Eng.*, H. Kolbel, M. Ralek.

Poutsma (M. L. Poutsma, ORNL--5635, 1980, "Assessment of Advanced Process Concepts for the Liquefaction of Low $H_2$/CO Ratio Synthesis Gas").

Deckwar (*Industrial Engr. Chem. Process Design Developments*, 1982, vol. 2, pp. 222, 223).

(C. N. Satterfield, G. A. Huff, J. G. Longwell, *Ind. Eng. Chem. Proc. Des. Dev.* 1982, 21, 465).

*Primary Examiner*—W. J. Shine
*Attorney, Agent, or Firm*—Willard Jones, II; James C. Simmons; E. Eugene Innis

[57] ABSTRACT

A catalyst is described for the synthesis of hydrocarbons from CO+$H_2$ utilizing a porous $Al_2O_3$ support impregnated with iron and copper and optionally promoted with an alkali metal. The use of an $Al_2O_3$ support results in the suppression of heavy waxes ($C_{26}+$ hydrocarbons), particularly in slurry phase operation, when compared to unsupported or co-precipitated catalysts.

15 Claims, No Drawings

METHODS FOR MAKING A SUPPORTED IRON-COPPER CATALYST

This invention was made under DOE contract No. DE-AC-80PC30021 and is subject to goverment rights arising therefrom.

FIELD OF THE INVENTION

This invention pertains to a catalytically active composition, to a method for making that composition and to a method for using that composition in the conversion of carbon monoxide to $C_1$-$C_{25}$ hydrocarbons with reduced $C_{26}+$ by-product.

The conversion of CO + $H_2$ to hydrocarbon products over a metal catalyst produces molecules with carbon numbers typically in the range 1–40 and higher. Since the reaction (sometimes referred to as a "Fischer-Tropsch" or "F-T" synthesis or process) involves a surface polymerization, the selectivity to a desired product range, e.g., $C_9$-$C_{25}$ (a fraction ideal for diesel fuel) is governed by the Schulz-Flory polymerization model. This model is characterized by a chain growth probability factor, $\alpha$, which determines the selectivity for a given range. If the probability of incorporation of an additional carbon atom into the growing chain is independent of the chain length, then the product distribution is defined by the following equation:

$$\log(W_i/C_i) = (\log\alpha)C_i + 2\log(1-\alpha)$$

Where $W_i$ is the weight fraction of the product with carbon number $C_i$, and $\alpha$ is the probability of chain growth, with values of 0–1. If this type of distribution is followed, a plot of log $(W_i/C_i)$ vs. $C_i$ produces a straight line with a negative slope of log $\alpha$.

This unselective polymerization process has significant implications for the maximum yield of transportation fuel product fractions; these are listed in Table 1.

TABLE 1

| Schulz-Flory Maximum | Schulz-Flory Product Fractions | | | | |
|---|---|---|---|---|---|
| | Alpha | $C_1$ | $C_5$-$C_{11}$ | $C_9$-$C_{25}$ | $C_{26}+$ |
| | | weight % | | | |
| Gasoline Range | 0.76 | 5.8 | 47.6 | 31.8 | 0.7 |
| Diesel Range | 0.88 | 1.4 | 31.9 | 54.1 | 12.9 |

This suggests that to obtain the maximum diesel range selectivity of 54.1%, 12.9 wt. % waxes ($C_{26}+$ hydrocarbons) must also be produced. These materials (the $C_{26}+$ fraction) have little or nor product value and generally must be further refined or converted.

Work on the Fischer-Tropsch synthesis is voluminous, and most previous work has involved fixed bed, gas/solid reactions. Early work was reviewed by Storch and Columbic (H. H. Storch, N. Columbic, R. B. Anderson, "The Fischer-Tropsch and Related Syntheses", Wiley 1951.). Slurry phase Fischer-Tropsch synthesis carried out more recently has been reviewed by Kolbel and Ralek (H. Kolbel, M. Ralek, *Catal. Rev. Sci. Eng.*, 1980, 21, 225), Poutsma (M. L. Poutsma, ORNL-5635, 1980, "Assessment of Advanced Process Concepts for the Liquefaction of Low $H_2$/CO Ratio Synthesis Gas ") and Deckwer(*Industrial Engineering Chemical Process Design Developments*, 1982, Vol. 2. p. 222, 223). Satterfield, et. al., recently examined literature on product distributions in Fischer-Tropsch synthesis, particularly in slurry reactors using Fe catalysts (C. N. Satterfield, G. A. Huff, J. P. Longwell, *Ind. Eng. Chem. Proc. Des. Dev.*, 1982, 21, 465). All these analyses indicate that the product selectivity follows a predicted Schulz-Flory distribution as described above. Because of this, the yields of $C_{26+}$ hydrocarbons obtained are high when $C_9$-$C_{25}$ fraction is optimized.

A variety of catalysts have been used in such processes including an iron-copper catalyst promoted with (but not supported on) $Al_2O_3$. (Reaction Kinetics and Catalysis Letters, 17, No. 3–4, 373 (1981)).

To maximize yield of transportation fuel product fractions, such as a $C_9$-$C_{25}$ fraction useful as diesel fuel, there is a need to improve the carbon monoxide polymerization and hydrogenation process in order to produce disproportionally less hydrocarbon fraction outside of the desired range, such as particularly the $C_{26}+$ fraction.

It is a general object of the present invention to meet that need by the provision of an improved catalyst, including methods for making and for using that catalyst in a Fischer-Tropsch reaction, by which the fraction of $C_{26}+$ by-product is reduced.

BRIEF DESCRIPTION OF THE INVENTION

The general object is met by a composition consisting essentially of alumina particles including on the surface thereof iron and copper, typically in oxide form, the copper and iron comprising, by weight of the composition, 0.1–5% and 1–30% respectively. Preferably, this catalytic composition is produced by depositing on the surface of porous particles, copper and iron precursor compounds, such as copper nitrate and iron oxalate or iron nitrate. Optionally, the catalytic activity may be enhanced by depositing also an alkali metal compound. In each case, the precursor compounds are converted to the oxides of the respective catalytic metals by drying after impregnation or deposition and then calcining in air (or some other oxygen-containing atmosphere). Preferably also, deposition of copper hydroxide and/or iron hydroxide is effected by contacting the alumina particles with a solution of copper nitrate and/or iron nitrate and then raising the pH of the solution. In that form of the invention in which iron nitrate is not co-precipitated with copper, the iron may be subsequently deposited by deposition or surface coating of the particles with a dry iron precursor compound, e.g. iron oxalate. This compound may be deposited by intergrinding with the copper impregnated alumina. The optional alkali metal addition, preferably potassium, may comprise up to about 2% by weight of the composition.

Preferably, the copper, iron and potassium contents of the composition are in the ranges, in percent by weight, of 0.1–1%, 10–20%, and 0.2–1% respectively.

For a better understanding of this invention reference may be had to the detailed description which follows, taken together with the subjoined claims.

DETAILED DESCRIPTION OF THE INVENTION

In its broadest sense, the present invention comprises an improved, catalyzed Fischer-Tropsch reaction process wherein carbon monoxide is polymerized and hydrogenated to form $C_1$-$C_{25}+$ hydrocarbons. The specific improvement of this invention is to reduce disproportionately the production of $C_{26}+$ hydrocarbons in this process by effecting the process in the presence of a catalyst comprising a composition made by depositing on or impregnating a porous alumina substrate material with catalytic metal precursors, particularly copper and iron precursor compounds convertible upon calcining to copper oxide and iron oxide. Optionally, the catalyst is further enhanced by deposition also of an alkali metal compound, such as potassium carbonate or bicarbonate.

Within the broad and preferred ranges of catalytic metal content set forth in the Brief Description of the Invention above, this catalytic composition may be produced in any of various sequences of deposition of precursor compounds and calcining. The catalytic composition is then activited for use in the Fischer-Tropsch process in a conventional manner by gradually exposing it to elevated temperature and pressure under reducing conditions, such as in a hydrogen or synthesis gas atmosphere, until it reaches the elevated temperature and pressure conditions desired for Fischer-Tropsch synthesis.

While any of a wide variety of alumina substrate material may be used, porous alumina, having a relatively high surface area, (preferably at least 75 square meters per gram) is preferred. One such substrate material is that commercially available from Rhone-Poulenc under the trade designation SCS-59. The method by which the various catalytic metal precursors may be deposited on the alumina substrate varies from chemical precipitation, to intergrinding in dry form, and to solution deposition by contact of the substrate with a solution, such as a solution of potassium carbonate, to the point of incipient wetness in accordance with conventional techniques. Where chemical precipitation is used, such as in the contact of the alumina substrate particles with a solution of copper nitrate and/or iron nitrate, the respective copper nitrate and/or iron nitrate is precipitated by neutralizing the solution with a base material such as ammonium hydroxide. By way of further example, a dry iron precursor material, such as iron oxalate for example, may be deposited by intergrinding in the dry state with the alumina particle substrate.

Any of a wide variety of other catalytic metal precursor materials may be used in this manner, the precursor compound in each case, however, necessarily being convertible upon calcining to the metal oxide or free metal state.

In addition to iron nitrate and iron oxalate, other typical iron precursor compounds include iron acetate, iron benzoate, iron sulfate, iron maleate, iron citrate, iron gluconate, iron lactate, iron oxide and hydrated iron oxide. Similarly, other possible copper precursor compounds (in addition to copper nitrate) include copper oxide and the oxalate, acetate, benzoate, sulfate, maleate, citrate, gluconate, and lactate salts of copper. Any of these compounds and combinations of these compounds may be used to the extent iron or copper can be deposited within the desired concentration range.

In one preferred deposition sequence, copper nitrate is first deposited by chemical precipitation onto an alumina porous substrate and calcined to produce copper oxide. Iron oxalate is then deposited by intergrinding (with the copper-alumina substrate) and calcined to produce free iron in combination with the copper oxide. Preferably also, the alkali metal enhancer is deposited by impregnation with a potassium carbonate solution to the point of incipient wetness, prior to the deposition of the iron precursor compound.

While not wishing to be bound to any particular theory of why the present invention works, it has been suggested that the catalyst of the present invention limits the amount of $C_{26}+$ or wax fraction in the hydrocarbon conversion by one of two possible mechanisms: (1) The FeCu particles are confined to the pores of the alumina resulting in a smaller and more uniform particle size distribution of catalytic particles, which has in turn been suggested in the literature as a means for limiting chain growth and thus production of higher molecular weight hydrocarbons; (2) the formation of heavy waxes occurs initially, and the waxes are absorbed in the pores of the catalytic substrate resulting in a high equilibrium concentration of the waxes around the catalyst particles, thus shifting the equilibrium to lighter products.

In any event, following are several descriptive examples of the invention, including use of the catalyst of the present invention in an improved carbon monoxide polymerization and hydrogenation process, conducted in slurry phase. For comparison, as set forth in Example 3, a comparative process was also conducted using a similar catalyst, that is a catalyst utilizing the same catalytic metals in co-precipitated form but without the additional benefit of the alumina substrate or carrier. The results of this comparison are shown in Table 4.

EXAMPLE 1: Catalyst Preparation

As described more fully below, a catalyst was prepared on a Rhone-Poulenc SCS-59 porous alumina substrate with a total final metal loading or content of 15% comprising 14% Fe, 0.5% Cu and 0.5% K, all by weight.

Copper was precipitated as $Cu(OH)_2$ from a solution of $Cu(NO_3)_2$ at pH=7 onto the SCS-59 $Al_2O_3$ by addition of $NH_4OH$ to the solution. The precipitate was then calcined in air at 800° C. for 3 hours, following which potassium was added as an aqueous solution of $K_2CO_3$ to incipient wetness. The resulting mixture was calcined at 500° C. $FeC_2O_4$ (iron oxalate) was then added to the $CuK/Al_2O_3$ by dry grinding.

An alternate method of preparation is to precipitate the metal hydroxides from solutions of $Fe(NO_3)_3$ and $Cu(NO_3)_2$ onto the support simultaneously. Promotion with potassium is not always required.

EXAMPLE 2

The catalyst prepared in Example 1 was activated in helium at 500° C. This resulted first in the decomposition of the oxalate to free iron. Table 2 summarizes the results of the gas phase screening studies using this catalyst. Catalyst activites were 320-400 kg CO converted/$m^3$/hour. The product distributions obtained did not conform to that predicted by the Schulz-Flory formula in that very low $C_{26}+$ fractions were produced.

EXAMPLE 3

A similar activation procedure was used for another sample of the $FeCuK/Al_2O_3$ catalyst produced as described in Example 1, for use in a slurry phase reaction. The catalyst was prepared using SCS-59 $Al_2O_3$ and $Fe(C_2O_4)$, with a metal loading in the following ratio: 11% Fe, 0.5% Cu, 0.5% K. The activation was carried out in a fixed bed reactor. The catalyst was heated to 500° C. in helium until CO and $CO_2$ were no longer observed in the gas. The catalyst was then contacted with a 1:1 molar ratio $CO/H_2$ mixture, at 300 psig, GHSV (Gas Hourly Space Velocity) = 700 and T = 275° C. Without exposure to air, the catalyst was then slurried in deoxygenated paraffin oil produced by Fisher Scientific and loaded into the slurry reactor. The slurry contained 17.8 wt. % catalyst. The results of the slurry testing are given in Table 3. The product distribution differs from the expected Schulz-Flory distribution only by the disproportionately small amount of $C_{26}+$ product. This is apparently due to use of the catalyst of the present invention. Consistent with this result, no increase in slurry level was observed in the reactor over the time of the test. The amount of slurry recovered at the end of the run after 552 hours continuous operation, was within 4% of the intial amount charged to the reactor.

Table 4 shows the results of a comparative test in which an uncalcined FeCuK catalyst prepared by co-precipitation without alumina or any substrate material, gave significantly more wax than the $Al_2O_3$ supported catalyst of the present invention. This comparative catalyst and its method of preparation is disclosed and claimed in a co-pending U.S. Patent Application (of common assignment herewith) Ser. No. 709,157, filed Mar. 7, 1985.

TABLE 2

Gas Phase Screening Results - Fe/Cu/$Al_2O_3$ Catalysts

| Catalyst Composition (wt %) | | | T (°C.) | P (psig) | CO/$H_2$ | GHSV | Conv. | Product Distribution (wt %) | | | | | |
|---|---|---|---|---|---|---|---|---|---|---|---|---|---|
| Fe | Cu | K | | | | | | $C_1$ | $C_2$-$C_4$ | $C_5$-$C_{11}$ | $C_9$-$C_{25}$ | $C_{26}+$ | Oxygenates |
| 14 | 0.5 | 0 | 274 | 300 | 1.04 | 1036 | 50 | 10.2 | 30.3 | 38.6 | 20.1 | 0.2 | 7.2 |
| 14 | 0.5 | 0 | 275 | 300 | 0.93 | 537 | 48 | 6.7 | 18.4 | 25.3 | 53.3 | 0 | 3.01 |
| 14 | 0.5 | 0.5 | 276 | 300 | 0.95 | 1167 | 55 | 7.1 | 21.23 | 31.4 | 44.5 | 0.6 | 5.6 |

TABLE 3

Results of Slurry Phase Testing - FeCuK/$Al_2O_3$

| T (°C.) | P (psig) | GHSV | CO/$H_2$ | CO Conv. | Product Distribution | | | |
|---|---|---|---|---|---|---|---|---|
| | | | | | $C_1$ | $C_5$-$C_{11}$ | $C_9$-$C_{25}$ | $C_{26}+$ |
| 258 | 303 | 313 | 2.0 | 9.5 | 12.6 | 22.2 | 36.7 | 0.5 |
| 260 | 495 | 305 | 0.93 | 13.7 | 13.0 | 42.4 | 22.4 | 0.0 |
| 278 | 742 | 258 | 2.0 | 13.9 | 11.9 | 38.8 | 29.4 | 0 |
| 280 | 300 | 315 | 1.0 | 10.3 | 14.5 | 33.3 | 23.4 | 0.7 |
| 302 | 750 | 289 | 0.93 | 32.0 | 16.0 | 35.9 | 16.6 | 0.2 |

TABLE 4

(Comparative)
Slurry Phase Testing Results
Co-Precipitated FeCuK (No Alumina)

| T (°C.) | P (psig) | GHSV | CO/$H_2$ | CO Conv. | Product Distribution | | | |
|---|---|---|---|---|---|---|---|---|
| | | | | | $C_1$ | $C_5$-$C_{11}$ | $C_9$-$C_{25}$ | $C_{26}+$ |
| 237 | 300 | 299 | 1.01 | 17.4 | 2.9 | 11.5 | 49.8 | 30.5 |
| 239 | 305 | 298 | 1.56 | 20.3 | 3.1 | 9.5 | 55.4 | 29.4 |
| 260 | 308 | 295 | 1.56 | 45.5 | 4.3 | 22.4 | 48.1 | 20.0 |

STATEMENT OF INDUSTRIAL UTILITY

This invention may be used in the conversion of coal, through gasification and Fischer-Tropsch synthesis, to hydrocarbon fuels. A higher proportion of diesel fuel range hydrocarbons ($C_9$-$C_{25}$) are produced by suppression of the production of $C_{26}+$ products or heavy wax. In accordance with the present invention, this results from conducting the carbon monoxide Fischer-Tropsch hydrogenation and polymerization reaction in the presence of a catalyst made by depositing iron and copper presursor compounds, on a finely divided porous alumina substrate.

We claim:

1. A method for making a catalytically active composition for Fischer-Tropsch reaction processes comprising:
    (a) depositing by chemical precipitation a solution of a copper-containing compound onto an alumina porous substrate;
    (b) calcining said depositing copper-containing compound on alumina substrate to form copper oxide on alumina substrate;
    (c) depositing by intergrinding an iron-containing compound with said copper oxide on alumina substrate; and
    (d) calcining the interground mixture in an inert atmosphere to produce free iron in addition to the copper oxide on the alumina substrate.

2. The method of claim 1 wherein said alumina substrate has a surface area of at least 75 square meters/gram.

3. The method of claim 1 wherein said copper compound comprises 0.1 to 5.0 percent by weight, based on metallic copper, and said iron compound comprises 1.0 to 30.0 percent by weight, based on metallic iron, of the catalytically active composition.

4. The method of claim 1 wherein said copper containing compound is copper nitrate.

5. The method of claim 1 wherein said iron containing compound is iron oxalate.

6. The method of claim 1 wherein said copper containing compound is copper nitrate and said iron containing compound is iron oxalate.

7. A method for making a catalytically active composition for Fischer-Tropsch reaction processes comprising:
    (a) depositing by chemical precipitation a solution of a copper-containing compound onto an alumina porous substrate;
    (b) calcining said deposited copper-containing compound on alumina substrate to form copper oxide on alumina substrate;
    (c) depositing by incipient wetness technique a solution of an alkali metal containing compound onto the calcined copper oxide on alumina substrate;
    (d) calcining the alkali metal compound and copper oxide on alumina substrate;
    (e) depositing by intergrinding an iron-containing compound with said copper oxide on alumina substrate; and
    (f) calcining the interground mixture in an inert atmosphere to produce free iron in addition to the copper oxide and alkali metal oxide on the alumina substrate.

8. The method of claim 7 wherein said alumina substrate has a surface area of at least 75 square meters/gram.

9. The method of claim 7 wherein said copper compound comprises 0.1 to 5.0 percent by weight, based on metallic copper, and said iron compound comprises 1.0 to 30.0 percent by weight, based on metallic iron, of the catalytically active composition.

10. The method of claim 7 wherein said copper containing compound is copper nitrate.

11. The method of claim 7 wherein said iron containing compound is iron oxalate.

12. The method of claim 7 wherein said alkali metal is potassium.

13. The method of claim 12 wherein potassium comprises up to 2.0 percent by weight, based on metallic potassium, of said catalytically active composition.

14. The method of claim 7 wherein said alkali metal containing compound is potassium carbonate.

15. The method of claim 7 wherein said copper containing compound is copper nitrate, said iron containing compound is iron oxalate, and said alkali metal containing compound is potassium carbonate.

* * * * *